US005458936A

United States Patent [19]

Miller et al.

[11] Patent Number: 5,458,936
[45] Date of Patent: Oct. 17, 1995

[54] POLYESTERURETHANE CONDOM

[75] Inventors: Robert G. Miller; Oskar T. Tankovitz, both of North York, Canada

[73] Assignee: Ortho-McNiel, Inc., Ontario, Canada

[21] Appl. No.: 159,017

[22] Filed: Nov. 29, 1993

[51] Int. Cl.⁶ .......................... A61B 19/00; B29D 22/00
[52] U.S. Cl. ...................... 428/35.7; 428/35.7; 128/918; 128/844; 604/349; 604/265
[58] Field of Search ........................... 428/35.7; 128/918, 128/844; 604/349, 265; 528/79, 76, 80, 83, 66; 525/440, 445, 920; 522/90

[56] References Cited

U.S. PATENT DOCUMENTS 4,576,156  3/1986  Dyck et al. .......................... 128/132 R

FOREIGN PATENT DOCUMENTS

0308683A1  8/1988  European Pat. Off. ..
WO90/05506  5/1990  European Pat. Off. ..

*Primary Examiner*—Charles R. Nold
*Attorney, Agent, or Firm*—John W. Harbour

[57] ABSTRACT

A condom of thermoplastic elastomer is drawn from a polyesterurethane.

1 Claim, 7 Drawing Sheets

5,458,936

POLYESTERURETHANE CONDOM

This invention relates to a method for making a non-rigid, flexible, thin walled, closed-ended, tubular article of thermoplastic elastomer, to an apparatus therefor and to the article produced. More particularly, this invention relates to a method for drawing, with a plug assist, very thin walled, non-rigid, flexible, closed-ended, tubular articles of thermoplastic elastomer, to a plug assisted drawing apparatus therefor and to liners, condoms and finger cots produced thereby.

BACKGROUND OF THE INVENTION

Thin walled tubular articles of thermoplastic elastomer are known in the art to provide strong, thin, flexible protective barriers. Protective barriers having these characteristics are particularly useful to protect skin surfaces from unwanted contact or contamination and, yet, to preserve sensitivity of touch, as with condoms or finger cots used in medical examination.

U.S. Pat. No. 4,576,156, Dyck, et al., describes a condom manufactured from a variety of polyurethane thermoplastic elastomers. In the process for manufacture, a shaped mandrel is urged into the face of pre-heated, extruded elastomeric film and the film assumes the shape of the mandrel with the application of vacuum.

U.S. Pat. No. 4,684,490, Taller, et al., describes a condom manufactured from certain polyurethane thermoplastic elastomers. In the process for manufacture, a mandrel is coated with an emulsion of elastomeric material prepolymer and the coating is cured at elevated temperature.

Additional methods to manufacture condoms from thermoplastic elastomers are generally known. In one process for manufacture, the thermoplastic elastomer is blown into very thin film, the film is cut into appropriate preforms and the segments are heat sealed to form a condom.

Despite the fact that thermoplastic elastomers are taught to be suitable materials for the manufacture of the articles described above; despite the fact that these elastomers may be employed to produce a stronger, thinner and a more reliably defect free product as compared to natural rubber, the present material of choice; thin walled tubular articles are not commercially produced from thermoplastic elastomers. Each of the above described processes is unsuitable for high volume production for one or more of several reasons. For instance, the wall thickness of the resultant product may not be controllable to the desired tolerance. Also, though the product is thinner and stronger, the elastomeric modulus may be too high, i.e., the elastomer may be too stiff. Further, considering cure or annealing times required, the through-put of the machinery required may be too low.

Thus, it is an object of the present invention to rapidly produce tubular articles of thermoplastic elastomer which are soft, flexible and have a uniformly thin wall thickness.

It is also an object of the present invention to provide a method for melt forming tubular articles of thermoplastic elastomer which have a low modulus and a uniformly thin wall thickness.

It is a further object of the present invention to provide a method and hardware to draw with plug assist, tubular articles of thermoplastic elastomer which have a low modulus and a uniformly thin wall thickness.

It is another object of the present invention to provide a thermoplastic elastomer which may be drawn into tubular articles having thin walls and a low modulus.

SUMMARY OF THE INVENTION

Briefly, according to the present invention, there is provided a method for making a thin walled, closed-ended, tubular article of a thermoplastic elastomer, said method comprising:

a) providing a tubular mold having a longitudinal axis, a terminal end, and an opposite open end, said open end having a rim, and providing a preform of thermoplastic elastomer, said preform having two opposing, substantially coplanar faces and said thermoplastic elastomer heated to have a viscosity and elasticity within a range that the preform can be drawn;

b) placing a face of said preform of thermoplastic elastomer on said rim;

c) applying air pressure or vacuum to one face of said preform to impose an air pressure differential across the faces of the preform and axially directing a plug against the outward face of the preform, thereby drawing and urging the preform to flow into the mold, the plug directed at a rate upon contact with the preform that the preform is not punctured by the plug;

d) further applying air pressure or vacuum and further axially directing the plug against the preform, the air pressure or vacuum applied at a rate and the plug directed at a rate whereby the resultant air pressure differential across the faces of the preform maintains a portion of the flowing preform away from the wall of the tubular mold; and e) at a point where the plug nears the terminal end, evacuating remaining air from between the flowing preform and the walls of the mold whereby the preform is drawn into contact with the cooling walls of the mold to form a shaped article.

Also provided by the present invention is a method to prepare a thermoplastic elastomeric preform for forming or drawing into a thin walled, closed-ended, tubular article having a wall thickness of between about 0.005 and 0.25 mm, said method comprising:

i) providing a tubular mold having a longitudinal axis, a terminal end, and an opposite open end, said open end having a rim;

ii) heating a thermoplastic elastomer to a sufficient temperature to substantially eliminate the crystalline regions, whereby the viscosity and elasticity of said thermoplastic elastomer are substantially reduced, and shaping said thermoplastic elastomer to form a preform having two substantially coplanar opposing faces;

iii) cooling said thermoplastic elastomer whereby the viscosity and elasticity are recovered within a range that the preform can be drawn; and iv) placing a face of said preform of thermoplastic elastomer on said rim.

Further provided by the present invention is a plug assembly for use in plug assisted drawing of thin walled, closed-ended, tubular articles of thermoplastic elastomer comprising an axially centered rod, said rod attached to the base of an axially centered, frustoconically shaped plug, said plug having a crown face opposite said base and extending from said crown face, an axially centered contact projection.

Further provided by the present invention is a plug assembly for use in plug assisted drawing of thin walled, closed-ended, tubular articles of thermoplastic elastomer comprising an axially centered rod, said rod attached to a first face of an axially centered, disc shaped plug, said plug having a second face opposite said first face and extending from said second face, an axially centered contact projection.

Also provided by the present invention is a condom formed from a polyesterurethane thermoplastic elastomer, said elastomer characterized by a melt index, measured at 210° C. under a 3800 g load, in the range of from 24–36 g/10 min; 10–25% by weight MDI; 0.1–5% by weight 1,4-butanediol; 70–89.9% by weight polybutylene/hexylene adipate having an average molecular weight of 1000–3000 Daltons; and 0–5% by weight lubricant.

Further provided by the present invention is a condom of thermoplastic elastomer, said condom having an axially centered tubular body, an open end and an opposite closed end, said tubular body having a maximum diameter at a point along said axis adjacent to said closed end and said tubular body having a minimum diameter at a point along said axis between said point of maximum diameter to and including said open end.

Additionally, provided by the present invention is a method to lower the modulus of a thin walled, closed-ended, tubular article of thermoplastic elastomer, said method comprising the steps of:

1) stretching said tubular article onto a forming mandrel; and
2) heating said tubular article and mandrel to a temperature of between 100° and 125° C. for a time sufficient to lower the modulus of said thermoplastic elastomer.

DETAILED DESCRIPTION OF THE INVENTION

Figure 1A:
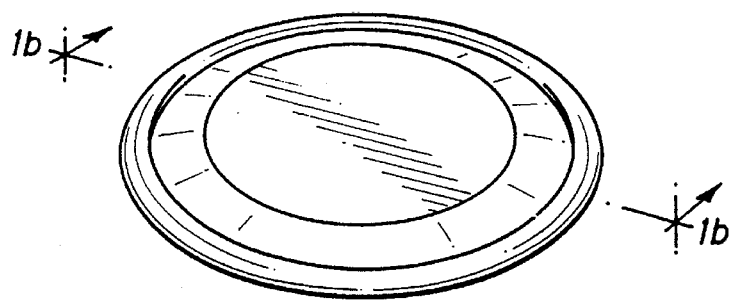
FIG. 1a is an isometric drawing of a rimmed preform having a flat profile.
Figure 1B:
FIG. 1b is a side centerline cross section of a rimmed preform having a flat profile.
Figure 2A:
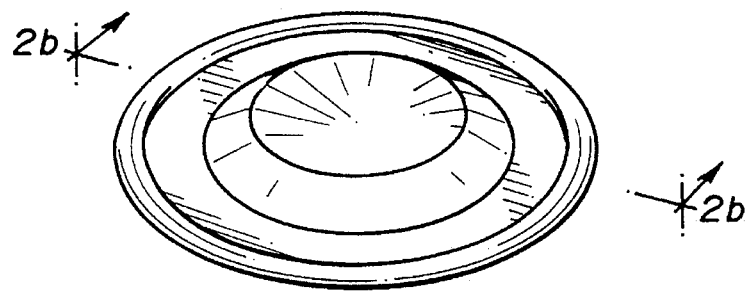
FIG. 2a is an isometric drawing of a rimmed preform having a profile.
Figure 2B:
FIG. 2b is a side centerline cross section of a rimmed preform having a profile.

The present invention is directed to thin walled, closed-ended, tubular articles of thermoplastic elastomers, to a process for making the same and to machinery therefor. Of course, the thinner the walls of the tubular article, the more critical are the instant materials and processes. Broadly, the instant invention is intended to produce a uniformly thin walled tubular article having a wall thickness of from about 0.005 mm to about 0.25 mm of thermoplastic elastomer and a length to diameter ratio of 2/1 to 20/1. The invention is most beneficially employed where the desired wall thickness is between about 0.01 mm and about 0.10 mm and the length to diameter ratio is 3/1 to 10/1. Prior to the present invention, thermoplastic elastomers could only be cast from solvents to uniformly produce wall thicknesses in this range.

Thermoplastic elastomers are block copolymers having hard and soft blocks, or domains, in the polymer molecule, or compound. The soft domains provide the rubber like elastomeric properties while the hard or crystalline domains act as mechanical crosslinks, tying down the rubbery domains. At processing temperatures, the hard domains of the thermoplastic elastomer become amorphous or soften to yield a melt that can be easily processed by injection molding, extrusion, vacuum molding, etc.

Suitable thermoplastic elastomers herein include polyurethanes, polyetherurethaneureas, polyetherurethanes, polyesterurethanes, polyester/polyether block copolymers, styrene/diene/styrene block copolymers, etc. The present invention may be applied to a broad range of thermoplastic elastomers, as the suitability of any given thermoplastic elastomer is more appropriately judged based on its physical properties than on its particular type. Controlling the physical properties of any thermoplastic elastomer is an art specific to that thermoplastic elastomer. Broadly, it can be stated herein that the physical properties of any thermoplastic elastomer are dependent upon hard block type, soft block type, block arrangement in the polymer, average polymer molecular weight, average hard block content with average number of repeating units, average soft block content with average number of repeating units and the use of additives, particularly, waxes, to improve processability, and, possibly, impact modifiers, to improve tear strength. For use herein, a thermoplastic elastomer should have a Shore A hardness between about 60 and 80, and preferably, between about 60 and 75. The tensile stress of the thermoplastic elastomer at 100% elongation, commonly referred to as the 100% modulus, should be between about 50 and 600 psi, and preferably, between about 100 and 500 psi. The equivalent 300% modulus should be between about 450 and 1100 psi, and preferably, between about 500 and 900 psi. The ultimate elongation should vary in the range of from about 400% to 800% and the compression set, 24 hrs at 23° C., should be no more than 25%. Importantly, the thermoplastic elastomer should have excellent resistance to organic solvents. All of the above ranges, unless otherwise stated, are measured at 23° C.

It is another aspect of the thermoplastic elastomer herein that it should not have a distinct melting point. In the art of drawing or extruding thermoplastic elastomers, an indistinct melting point is one factor in having a melt which is formable, yet will retain a shape that it has been given.

Within the range of an indistinct melting point, a melt will exhibit a "green strength". An indistinct melting point is a characteristic of a melt containing a range of molecular weight polymers.

A preferred thermoplastic elastomer is a block copolymer of polyurethane hard blocks with polyester soft blocks. These thermoplastic elastomers have been found to have excellent physical strength, superior abrasion and tear resistance, and excellent tensile strength. In addition these thermoplastic elastomers show excellent resistance to organic solvents.

Low modulus and low set are achieved in the preferred polyesterurethane by selecting, as the soft block, a long chain diol or combination of diols, which tend to crystallize little at ambient temperature; and hard block content of no more than 25%. The rigid hard block is achieved by reaction of a polyisocyanate and a short chain diol.

10 to 25 weight percent of the preferred polyesterurethane is comprised of one or more polyisocyanates. Preferably the polyisocyanate is a diisocyanate. Useful diisocyanates include aromatic and aliphatic diisocyanates. Suitable diisocyanates include non-hindered aromatic diisocyanates such as: 4,4'-methylenebis-(phenyl isocyanate) (MDI); isophorone diisocyanate (IPDI), m-xylene diisocyanate (XDI), as well as non-hindered cyclic aliphatic diisocyanates such as 1,4-cyclohexyl-diisocyanate, naphthylene-1,5-diisocyanate, diphenylmethane-3,3'-dimethoxy-4,4'-diisocyanate, dicyclohexylmethane-4,4'-diisocyanate, and cyclohexyl-1,4-diisocyanate, as well as combinations thereof. The most preferred non-hindered diisocyanate is 4,4'-methylenebis-(phenyl isocyanate) i.e., MDI.

0.1 to 5 weight percent of the preferred polyesterurethane is comprised of chain extenders. Suitable chain extenders are lower aliphatic or short chain glycols having from about 2 to about 6 carbon atoms. Examples of suitable chain extenders include, for instance, diethylene glycol, propylene glycol, dipropylene glycol, 1,4-butane diol, 1,6-hexane diol, 1,3-butane diol, 1,5-pentane diol, 1,4-cyclohexanedimethanol, hydroquinone di(hydroxyethyl)ether, and the like, as well as combinations thereof, with 1,4-butane diol being preferred.

70 to about 89.9% by weight of the preferred polyesterurethane is comprised of a hydroxyl terminated polyester. A preferred class of hydroxyl terminated polyester intermediates is generally a linear polyester having a molecular weight of from about 500 to about 5,000 Daltons, and most preferably from about 1,000 to about 3,000 Daltons, and an acid number generally less than 0.8 and preferably less than 0.5. The molecular weight is determined by assay of the hydroxyl groups. The polyester intermediates are produced by (1) an esterification reaction of one or more glycols with one or more dicarboxylic acids or anhydrides, or (2) by transesterification reaction, i.e., the reaction of one or more glycols with esters of dicarboxylic acids. Mole ratios generally in excess of more than one mole of glycol to acid are preferred so as to obtain linear chains having a preponderance of terminal hydroxyl groups.

The dicarboxylic acids can be aliphatic, cycloaliphatic, aromatic, or combinations thereof. Suitable dicarboxylic acids which may be used alone or in mixtures usually have a total of from 4 to 15 carbon atoms and include: succinic, glutaric, adipic, pimelic, suberic, azelaic, sebacic, dodecanoic, isophthalic, terephthalic cyclohexane dicarboxylic, and the like. Anhydrides of the above dicarboxylic acids, such as phthalic anhydride, or the like, can also be utilized, with adipic acid being preferred.

The ester-forming glycols can be aliphatic, aromatic, or combinations thereof; have a total of from 2 to 12 carbon atoms; and include; ethylene glycol, 1,2-propylene glycol, 1,3-propanediol, 1,3-butylene glycol, 1,4-butanediol, 1,5-pentanediol, 1,6-hexanediol, 2,2-dimethylpropane-1,3-diol, 1,4-cyclohexanedimethanol, decamethylene glycol, dodecamethylene glycol, and combinations thereof. The combination of 1,4-butanediol with 1,6-hexanediol being the preferred glycol.

The preferred polyesters of the preferred polyesterurethane are mixed esters such as polybutylene/hexylene adipate, polybutylene adipate/azelate. The most preferred polyester is a polybutylene hexylene adipate.

In addition to the above polyester intermediates, numerous other types of polyester intermediates known to the art and to the literature can be utilized, including those having different molecular weights and/or contain branch polyesters therein. For example, polycaprolactone diols can be used. These are known polyester reaction products of lactones and bifunctional compounds having two reactive sites capable of opening the lactone ring. These bifunctional materials may be represented by the formula HX—R—XH wherein R is an organic radical which can be aliphatic, cycloaliphatic, aromatic or hetercyclic and X is O, NH and NR where R is a hydrocarbon radical which can be alkyl, aryl, aralkyl and cycloalkyl. Such materials include diols, diamines and aminoalcohols preferably. Useful diols include alkylene glycols wherein the alkylene groups contain 2 to 10 carbon atoms for examples, ethylene glycol, 1,2-propane diol, 1,4-butanediol, 1,6-hexamethylene diol and the like.

The intermediate, such as hydroxyl terminated polyester, is further reacted with one or more polyisocyanates and preferably a diisocyanate along with a chain extender, desirably in a "one-shot" process, that is, a simultaneous co-reaction of the intermediate, diisocyanate, and the chain extender, to produce a moderate molecular weight linear polyurethane having a melt index of from about 1 to about 150 and preferably from about 1 to about 75 at 2,160 grams test load. The equivalent amount of diisocyanates to the total amount of hydroxyl containing components, that is, the hydroxyl terminated polyester, and the chain extender, is from about 0.95 to about 1.13, and desirably from about 0.98 to about 1.06.

Alternatively, the urethane can be made in a conventional two-step process wherein initially a prepolymer is made from the polyisocyanate and the intermediate, with the prepolymer subsequently being reacted with the chain extender. The equivalent ratio of the one or more polyisocyanates to the hydroxyl terminated intermediate is generally a sufficient amount such that, upon subsequent chain extension with a suitable chain extender, the overall equivalent ratio of the hydroxyl terminated compound to one or more polyisocyanates is approximately 0.95 to about 1.065 and the like.

Examples of the above, as well as other suitable thermoplastic polyurethanes which can be utilized, are set forth in Vol. 13 of the Encyclopedia of Polymer Science and Engineering, John Wiley & Sons, Inc., New York, N.Y., 1988, pages 243–303, which is hereby fully incorporated by reference.

In addition, the polyurethane can be blended with various additives such as, for example, antioxidants, stabilizers, lubricants, process aids. Most preferably, the polyurethane is blended with 0 to about 5 weight percent of a lubricant composition. Any compatible or appropriate lubricant composition giving the desired characteristics can be used. Suitable examples include fatty bisamide or fatty esters.

The preferred polyesterurethane thermoplastic elastomer may be produced in a two step process. In a first polymerization, polyester blocks are produced by reacting the diol and the diacid to produce diol polyester blocks. In a second polymerization, the diol polyester blocks are reacted with a mix of diisocyanate and at least one diol monomer, the latter two in appropriate ratio to the polyester block and to each other to produce the desired molecular weight for the polymer and the hard blocks. However, the most preferred process for making the thermoplastic polyesterurethane is a "one shot" polymerization process. The diols, diisocyanate and chain extenders are reacted at a temperature above 100° C. and desirably above 120 ° C. The reaction is exothermic and results in the preferred polyesterurethane.

By way of example, a specific polyesterurethane thermoplastic elastomer, has a molecular weight in the range of from 145,000 to 190,000 Daltons, corresponding to a melt index, measured at 210° C. under a 3800 g test load, in the range of from 24–36 g/10 min; 10–25% by weight MDI; 0.1–5% by weight 1,4-butanediol; 70–89.9% by weight polybutylene/hexylene adipate having an average molecular weight of 1000–3000 Daltons; and 0–5% by weight lubricant. This specific polyesterurethane has the properties of Table I.

TABLE I

| Property Value | ASTM METHOD | |
|---|---|---|
| Hardness, Shore | D2240 | 74 A |
| Specific Gravity | D792 | 1.17 |
| DSC Thermal Transition Temperature, °C. | D3418 | |
| $T_g$ | | −40 |
| $T_{bc}$ | | −10 |
| $T_{bm}$ | | 27 |
| $T_m$(max) | | 165 |
| Stress-strain, psi | D412 | |
| 100% modulus | | 500 |
| 300% modulus | | 905 |
| ultimate tensile strength | | 5100 |
| ultimate elongation (%) | | 550 |
| Tear Strength, pli | D1938 | 244 |
| Compression Set, % | D395 | |
| 22 h/23 ° C. | | 23 |
| 22 h/70 ° C. | | 74 |

The articles of the present invention are formed from the thermoplastic elastomer, firstly, in a preform operation and, secondly, in a plug assisted drawing operation. In the preform operation, the thermoplastic elastomer is made into an appropriate preform and heated to a suitable temperature for plug assisted drawing. In the plug assisted drawing operation, the preform is drawn with a plug assist into the thin walled tubular articles herein. Finally, the articles may be annealed to remove residual stress.

At a minimum, it is required of the preform operation that a thermoplastic elastomer is heated to eliminate the crystalline phase and thereby, substantially, the elasticity; that the thermoplastic elastomer is shaped into a preform having essentially two opposing substantially coplanar faces; that the preform is cooled, recovering viscosity and elasticity within a range that the preform can be drawn; and that the preform is positioned over the mold cavity for drawing with plug assist. Each of these steps, without more, is well within the capabilities of the skilled artisan. However, disclosed as follows are preferred and contemplated methods for accomplishing each of these steps.

Physically, the preform may take a variety of shapes with the functional requirement being that the preform is useful in a plug assisted drawing apparatus of the type disclosed herein. As the necessary characteristic, the preform should have essentially two opposing substantially coplanar faces which, when restated, is intended to mean that the preform is a thin flat piece of thermoplastic elastomer. In its specific embodiments, the preform might be a square panel or a round disc which is cut and/or stamped from a larger extruded sheet or the preform might be a ribbon or sheet from which the article is cut at the time of plug assisted drawing. Of course, in either case, the extrusion, molding or stamping of the preform might be performed at the site of the plug assisted drawing operation and it may even be advantageous to integrate the two operations. The preform may simply have planar faces or the face of the preform may be profiled to obtain some advantage in thermoplastic elastomer melt distribution in the mold during the plug assisted drawing operation. Referring to FIGS. 1a and 1b and FIGS. 2a and 2b, there are shown possible disc-shaped preforms having a profiled surface which might be advantageously employed herein. Although it is well within the ability of a person skilled in the art to choose an appropriate shape and size for a preform given a particular product, it is recommended that preforms herein have a thickness no greater than about 5 mm and no less than about 0.5 mm, and preferably between 1 and 2.5 mm.

The preform should be heated to a forming temperature at which the rate of standing deformation is insufficient to substantially deform the preform during the time period of the preform operation, and at which the elasticity and viscosity of the melt is within the range that the preform can be drawn into a thin walled, closed-ended, tubular article. This range of elasticity and viscosity at which the melt can be drawn may be characterized in two ways. The first characteristic of this range is that, to as great a degree as possible, resistance to flow in the thermoplastic elastomer melt should be viscous and not elastic. The second characteristic of this range is that under the combined effect of viscosity and elasticity, the thermoplastic elastomer should not stick, tear or warp when drawn to the desired thickness. In the case of the polyesterurethane described above, the heating was carried out to a temperature between 190° and 210° C. and the melt was cooled for drawing to a temperature between 145° and 185° C. and preferably between 150° and 170° C. This temperature range for drawing corresponds roughly to a melt viscosity (i.e. complex viscosity), as measured with a Rheometrics Mechanical Spectrometer at the forming temperature, in the range of 75,000 to 150,000 Poise and an elastic modulus, at the forming temperature, in the range of from 600,000 to 1,200,000 dyne/cm$^2$.

As stated above, it is necessary to the process described herein that the elastomeric character of the thermoplastic elastomer be minimized for the plug assisted drawing operation. That is, the principal resistance to the initial deformation of the preform in the plug assisted drawing operation should be viscous resistance. This can be accomplished by substantially eliminating the crystalline domains through a controlled heat history of the thermoplastic elastomer. Simply, the thermoplastic elastomer should be first heated to a sufficient temperature to substantially eliminate the crystalline domains and, subsequently, cooled to the temperature of drawing. As crystalline domains do not immediately reform, there is some time period in which the thermoplastic elastomer may be deformed without substantial elastic resistance to deformation. It is preferred that the thermoplastic elastomer be immediately cooled and drawn with plug assist, since the reformation of the crystalline domains begins with cooling and proceeds until a crystalline domain content consistent with temperature is regained. For any given thermoplastic elastomer, and using the technique of first heating to eliminate the crystalline domains, it is a trivial matter to optimize the temperature to which the thermoplastic elastomer should be cooled for drawing. In one preferred method, a preform at room temperature is heated to a sufficient temperature to substantially eliminate the crystalline domains. In the short time period for which the preform is held at this temperature, the standing deformation of the preform is insignificant. Immediately, the preform is allowed to cool to the temperature of plug assisted drawing and drawn. In another preferred method, thermoplastic elastomer is heated to a sufficient temperature to substantially eliminate the crystalline domains and extruded into a ribbon preform. The preform is cooled to the temperature of plug assisted drawing and successive segments drawn.

Figure 3:
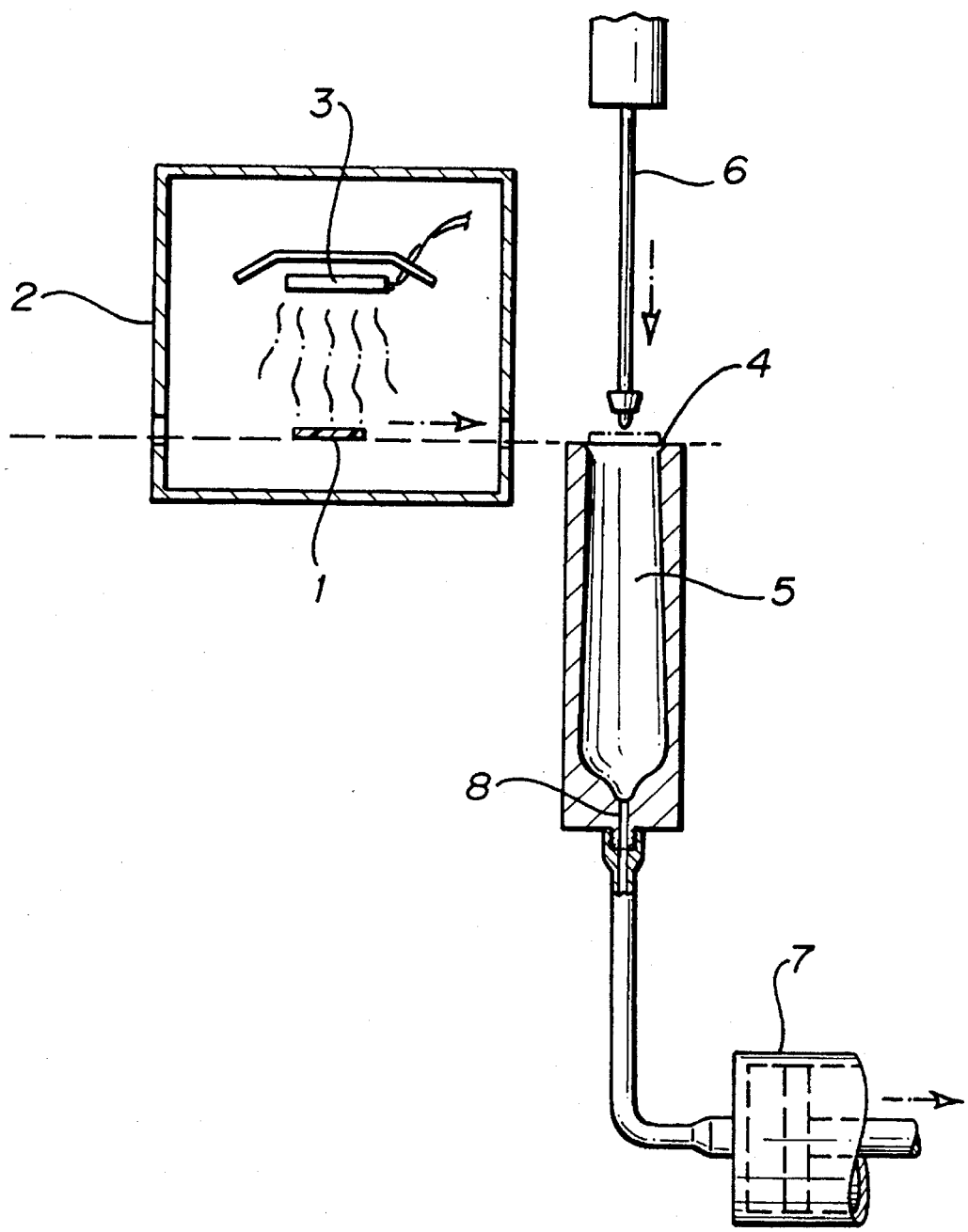
FIG. 3 is a schematic of a preheating and plug assisted vacuum drawing apparatus as taught herein.

The heating step of the preform operation might be carried out in an oven and/or extruder barrel. Referring to FIG. 3, in the instance where an oven is employed, it is suggested that the preform 1 is positioned in the oven 2 horizontally and heated by contact with hot air and exposure to an IR source. A suggested IR source might be nothing more sophisticated than the glowing elements of an electric resistance heater 3 or the IR souce may be a lamp designed to emit IR radiation. With the relatively thin preforms employed in the process herein and relying primarily on an IR heat source, the temperature of the preform can be rapidly changed to minimize standing deformation and to increase through-put. Where it is attempted to heat the preform at an incline or positioned vertically, the weight of the preform will aggravate standing deformation.

Additional and possibly more advantageous methods of heating the preform are contemplated. One possible method of heating the preform might utilize microwave radiation. In this case, an appropriately designed oven would be required, as well as dopants in the thermoplastic elastomer to convert the radiative energy to heat. In a second method of heating, the plug assisted drawing might be performed on a preform off an extruder where the preform has cooled to an appropriate temperature for drawing. In this case, there would be no need for a heat source other than the extruder.

The heating of the preform, as well as the controlled heat history are well within the skill of the art. Applicants have critically applied these techniques to the plug assisted drawing of tubular articles of thermoplastic elastomer.

As stated above, it is the purpose of the plug assisted drawing operation to mold the preform into the thin walled tubular articles herein. A first feature of the plug assisted drawing operation is the use of a plug assist, or mandrel, complementing the application of an air pressure differential across the faces of the preform to both urge and draw the heated preform into the mold. A second feature of the plug assisted drawing operation is the dynamic relationship of air pressure differential across the faces of the preform to plug extension into the mold.

In regard to imposing and controlling an air pressure differential across the faces of the preform, two techniques might be employed. In one technique, the pressure differential is the result of positive and negative guage pressure applied to the outward face of the preform with the mold cavity maintained at a constant pressure, preferably atmospheric. In a second technique, the pressure differential is the result of a positive and negative gauge pressure applied within the mold cavity, with the preform sealably mounted on the rim of the mold. Whether the preform is drawn into the mold with an air pressure differential created by an external positive pressure or internal negative pressure, it is considered herein to be "drawn". The two techniques are considered equivalent. The preferred technique for the description herein is the second technique where air pressure differential is controlled by applying vacuum to the mold. However, this is mainly due to the fact that the prototype machinery where air pressure diffential is controlled in this manner is simpler to build and operate.

Herein, the pressure differential across the faces of the preform will be stated as a positive value where the pressure is into the mold and as a negative value where the pressure is out of the mold. Thus, where a positive differential pressure is applied to the preform, it may be created by mold vacuum or by an external pressure. Similarly, where a negative differential pressure is applied, it may be the result of a pressurized mold or an external vacuum.

FIG. 3 depicts an embodiment of the present invention where air pressure differential is controlled from within the mold. Referring to FIG. 3, heated preform 1 is positioned on rim 4 of mold 5 with plug assembly 6 fully retracted, whereby the mold is sealed. With the mold sealed, air is evacuated from the mold by means of vacuum source 7 through vacuum port 8. Simultaneously or subsequently to the time that the air is drawn from mold 5, plug assembly 6 is extended into the mold to make contact with the preform and urge it into the mold. Through the combined effect of air evacuation and plug extension, the deformation of preform 1 into the mold is substantially accelerated. Plug extension rate and air evacuation rate combine to produce a dynamic mold pressure which, as described below, may alternatively assist or resist the action of the plug on the deforming thermoplastic elastomer. With the plug assembly fully extended, the remaining air in the mold is evacuated by means of vacuum source 7 and the molded article is removed. FIG. 3 may be modified to impose the air pressure differential with apparatus on the outward face of the preform. In this technique, a pressurizeable cavity may be brought into sealed contact with the outward face of preform 1, the contact opposite the rim 4. This pressurizeable cavity would have a sealed opening through which plug assembly 6 would extend and a pressure port to which the equivalent of vacuum source 7 would be attached. Vacuum port 8 could be open to the atmosphere.

As stated above, the process herein is most beneficially applied to tubular articles of thermoplastic elastomer having thin walls and a length to diameter ratio within the boundaries recited. Providing an appropriately sized mold in which to produce such an article is clearly within the skill of the art. Since the mold need not be heated or excessively pressurized, a variety of materials are available.

Figure 4A:
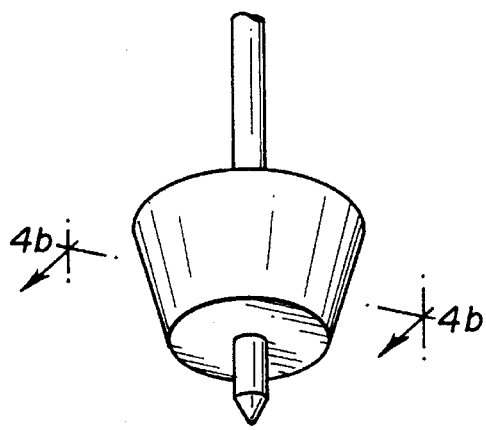
FIG. 4a is a isometric drawing of a plug assembly as taught herein.
Figure 4C:
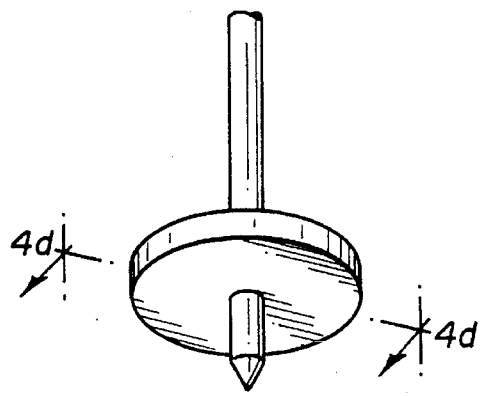
FIG. 4c is a isometric drawing of a plug assembly as taught herein.
Figure 4B:
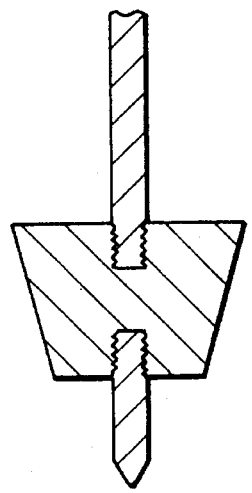
FIG. 4b is a side centerline cross section of a plug assembly as taught herein.
Figure 4D:
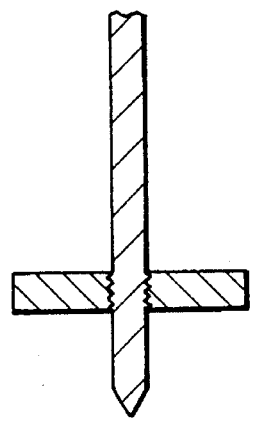
FIG. 4d is a side centerline cross section of a plug assembly as taught herein.

In regard to the first feature of the plug assisted drawing operation, the purpose of the plug assembly is to urge the deforming preform into the mold cavity and, in doing so, to bias the flow of the deforming thermoplastic elastomer preform axially along the mold cavity, avoiding contact with the mold walls until the point at which it is nearly fully drawn. The plug assembly comprises the plug itself attached at its base to a rod. The purpose of the plug is to provide a surface to contact the deforming preform. The rod provides a support on which to mount the plug and by which the plug may be extended into the mold cavity. The materials of manufacture and the shape of the plug may vary widely. Of course, any choice of materials and any plug design should have as objectives, that the material not stick to the hot preform, that surface area of contact be minimized at the same time that sufficient surface is presented to prevent inappropriate stress or punctures in the material, that contact with the plug minimize heat loss to the plug, etc. It is not an objective of the plug design to provide an appropriate surface against which to compressively shape the preform. The plug might be manufactured of non-stick polyolefins, such as, poly(perfluoro-olefins), e.g. teflon, or aluminum, optionally having a textured surface. The shape of the plug might be ellipsoidal, toroidal, paraboloidal, a segmented paraboloid with perpendicular bases, barrel shaped, spherical sector shaped, frustuconical (frustum of a right circular cone), cylindrical, etc. Referring to FIGS. 4a and 4b, a preferred plug is a frustoconically shaped plug having extending from its crown face, an axially centered contact projection. Referring to FIGS. 4c and 4d, another preferred plug is a truncated cylinder or disc having extending from a radial face, an axially centered contact projection. Also, it is preferred that the plug is made of a textured aluminum.

In the preferred method of using the plug assembly and mold, the mold is aligned along a vertical axis with the rim defining an opening centered about the axis on one end and the vacuum port located at the opposite, terminal end at a point where the terminal end intersects the vertical axis. The plug assembly is mounted along the vertical axis and the plug is extensible into the mold cavity along the vertical axis for substantially the length of the mold. It should be made clear that the plug is not a compressive member and, thus, should clear the rim, the mold walls and the terminal end of the mold by distances greater than the thickness of any thermoplastic elastomer with which it is in contact at that point. In line with this, the plug should only be capable of extending substantially the length of the mold clearing the terminal end, at least, not only by the distance just stated, but also by a sufficient distance that the drawn end of the preform is not prematurely entrained in flowing air as it exits the mold port in the final drawing step as described below.

The pressure or vacuum source is not critical herein. Persons skilled in the art will readily be able to choose a means for pressurizing air or drawing a vacuum from, for example, a vacuum reservoir maintained by an ejector or rotary compressor; a rotary compressor; or a single-stage, single-acting piston. The preferred pressure or vacuum source is the single-stage, single-acting piston connected to the pressure or vacuum port without a reservoir. Where such a piston is sized to a volume larger than the mold itself, then the mold may be filled or evacuated in a single draw of the piston and a discharge of the piston back into the mold at the end of the drawing operation will assist in clearing the mold for subsequent plug assisted drawing operations.

As restated from above, the second feature of the plug assisted drawing operation, is the dynamic relationship of air pressure differential across the faces of the preform in the mold to plug extension into the mold. This relationship of pressure differential as a function of plug extension can be divided into three separable stages over the length of plug extension.

The first stage is the relationship of air pressure differential to plug extension up to or about the time of contact between the preform and the extending plug. In the first stage, there is either a positive differential applied to the preform drawing it into the mold or a neutral or zero pressure differential is maintained and extension of the plug into the mold is begun. At the latest, it is necessary to control a positive pressure differential or actively maintain the neutral pressure differential at the point at which the extending plug makes contact with the preform and the preform is thereby urged into the mold. If controlling the pressure differential is delayed much after contact of the extending plug with the preform, a damaging pressure will build as the preform is urged into the mold against a sealed mold or external cavity. It is preferred in the first stage that a positve pressure differential is applied to the preform prior to contact between the extending plug and the preform. Specifically, sufficient pressure differential is applied and the rate of plug extension is set such that the preform is deformed by action of the pressure differential to a substantially hemispherical shape in the time between the application of the pressure differential and contact of the preform by the plug. It is preferred in this first stage that the preform be drawn by the pressure differential to a shape and given a momentum of deformation better suited for contact with the plug. Prior to plug contact with the preform, the pressure differential should at least be sufficient to deform the contacting face of the preform into a concave shape and preferably into a hemispherical shape. However, past the point at which the deformimg preform is hemispherical in shape, further deformation by the pressure differential alone will draw the body of the deforming preform into the tubular mold where continuous contact with the mold wall will be made as it is drawn. This contact with the mold wall produces thick nonuniform walls in the molded article for the length of such contact. Plug contact should therefor be made with the preform prior to a point at which the shape of the deforming preform is substantially tubular. Specifically as to the rate of plug extension in the first stage, it must clearly be axially greater than or equal to the axial draw rate of the deforming preform resulting from the pressure differential. However, the rate of plug extension should not be so great that upon contact with the preform, the preform is punctured. Suitably, the pressure differential in the first stage should range from 0 to 500 mm-Hg, and preferably from 5 to 200 mm-Hg. These pressures are not absolute pressures, but relative pressures where 0 mm-Hg is no pressure across the preform.

The second stage is the relationship of air pressure differential across the faces of the preform to plug extension from at or about the time of contact between the extending plug and the deforming preform to about the point at which the plug is fully extended. In this second stage, the air flow rate from the pressure or vacuum source is such that when combined with the extension of the plug into the mold, there results a pressure differential at or about 0 mm-Hg. It is desired in this second stage that the deforming preform be fully extended into the mold cavity with mold wall contact only in the area of the mold rim assembly. This can be accomplished where the plug is employed to urge the deforming preform into the mold cavity, biasing the flow of the deforming thermoplastic elastomer preform axially into the mold cavity, and the pressure differential is used to prevent contact between the drawn thermoplastic elastomer and the mold walls until about the point at which the plug is fully extended. By reducing the pressure differential to about 0 mm-Hg, the pressure which would otherwise urge the preform into the mold and, conmitantly, into the mold wall is equalized, with the result that thin walls of the drawn article are not pressed into the wall. By the drawing action of the plug, the thin walls of the drawn article are pulled nearly to a line extending from the trailing point of contact with the plug to the rim assembly. Further, by the action of hoop stress, which resists deformation in the drawn thermoplastic elastomer, the thin walls of the drawn article are pulled radially inward toward the axis of plug extension. Thus, a pressure differential of up to 25 mm-Hg and preferably up to 5 mm-Hg might be tolerated in the second stage depending on draw rates, thermoplastic elastomer, preform temperature, and so on. Also, depending on these same factors, a negative pressure differential might be advantageous in the second stage, with the pressure differential running from 0 to –25 mm-Hg and preferably from 0 to –5 mm-Hg. A negative pressure differential would tend to hold the thin walls of the drawn article radially inward and away from the mold wall. Of course, the negative pressure differential should not be so great that the thin walls of the drawn preform contact the rod of the plug assembly. In order to maintain the pressure differential within the desired ranges of the second stage, the volumetric displacement within the mold resulting from the axial extension of the plug and the drawn preform into the mold must be roughly balanced by the air flow rate from the vacuum or pressure source.

The third stage defines the relationship of air pressure differential across the faces of the preform to plug extension from at or about the point at which the plug is fully extended to the point at which the mold is fully evacuated and the preform is drawn into full contact with the mold walls. It is the purpose of the actions in the third stage to finally shape the thin walled tubular article. The plug is fully extended in the third stage. Air pressure differential is raised as necessary to evacuate the mold and bring the walls of the tubular article into deforming contact with the mold walls. Preferably, the action of raising the air pressure differential lifts the expanded preform from contact with the plug which permits an unentangled retraction of the plug. Contact of the expanded preform with the mold walls cools the resultant thin walled tubular article sufficiently that it may be removed from the mold.

In combining the three stages of plug extension and pressure differential into a single continuous drawing operation, there are several options. For a given mold volume, mold length, thermoplastic elastomer, etc., there is likely a constant plug extension rate which when combined with a constant rate of air flow from the pressure or vacuum source will result in a pressure differential and plug extension profile falling within the boundaries just described. Of course, while the resulting profile might be the most convenient from the point of view of equipment and operation, a superior product might be produced by having various plug extension rates and various rates of air flow to achieve the stated objectives of the three stages.

Thus, in a preferred embodiment, there is provided a method for making a thin walled tubular article of a thermoplastic elastomer, said method comprising:

a) aligning an elongated mold cavity along a substantially vertical axis, said elongated mold cavity defined by a mold comprising: a terminal end, having surfaces intersecting said vertical axis, radially defined sides, substantially parallel to said vertical axis, a working end, comprising a rim assembly defining an opening centered about said vertical axis, and means to evacuate said mold cavity, said means to evacuate comprising a port attached to said terminal end at a point where said terminal end and said vertical axis intersect, b) aligning a plug along said vertical axis, said plug extensible along said vertical axis through said opening into said mold cavity to a point substantially the length of said mold cavity, said plug clearing said rim assembly, said sides and said terminal end by distances substantially greater than the thickness of any contacted thermoplastic elastomer at that point;

c) positioning, said plug retracted, a substantially planar preform of thermoplastic elastomer across said opening, said preform having opposing top and bottom faces; said preform heated to a temperature at which the rate of standing deformation is insufficient to substantially deform the preform during the time period of said positioning step and at which the viscosity and elasticity are within a range that the preform can be drawn; and said preform radially extending from said vertical axis in a 360° arc to a point beyond said opening as defined by said rim assembly, whereby at least one face of said preform is in contact with said rim assembly, whereby said cavity is sealed, and whereby said incipient flow is along said vertical axis with the force of gravity;

d) applying an air pressure differential across said top and bottom faces of said preform and directing said plug along said vertical axis to contact a face of said preform, whereby the preform is drawn by said pressure differential and urged by said plug to flow along said vertical axis and into said cavity whereby the air of said mold cavity is evacuated through said port;

e) drawing and urging said preform into said mold for substantially the length of the mold cavity, where the rate of plug extension combined with the rate of air evacuation produces a pressure differential whereby the drawn and urged preform is held away from the mold walls, said plug extended to a point that the preform is not in contact with the terminal end of the mold; and g) evacuating the mold, whereby the preform is drawn into full contact with the cooling walls of said mold whereby a shaped article is formed.

Following the plug assisted drawing operation, it may be desirable to further modify the elastomeric properties of the drawn article by thermal annealing process. This type of process for a thermoplastic elastomer is described by Nallicheri, R. A. and Rubner, M. F., Macromolecules, 190, 23, 1005–1016. Basically, to remove residual stress in the vacuum drawn article and thereby lower modulus, the article is annealed by heating it at a moderate temperature for an extended period of time and, optionally, shaping it during heating by stretching it over a mandrel. In the case of polyesterurethane article, the annealing process might be carried out by simply heating, in a convection oven at 130° C. for 4 hours. Generally, an annealing process might be carried out at a temperature of from 100° C. to 140° C. for a time period ranging from 1 to 24 hours.

Figure 6:
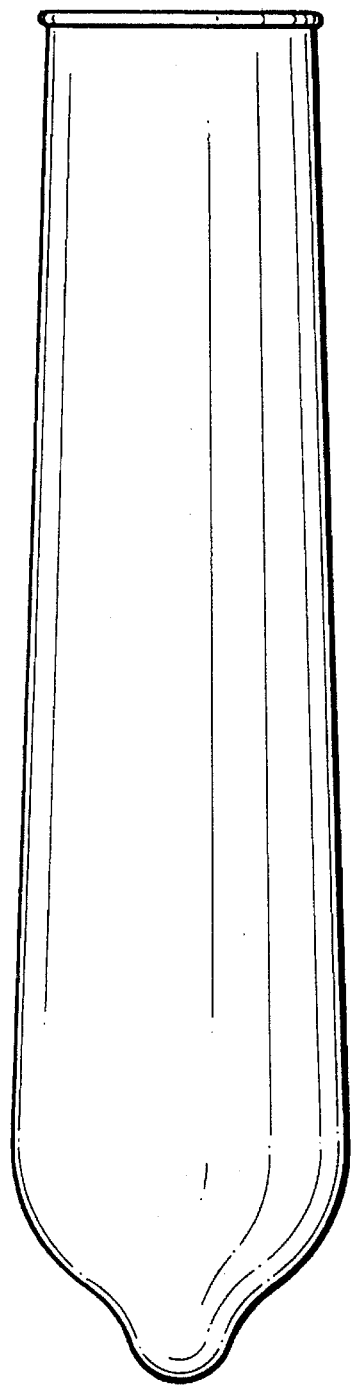
FIG. 6 is a tapered condom.

The process described herein is most advantageously employed to produce condoms or finger cots. In the case of condoms a molded article herein will have a length of from about 125 to about 225 mm and a diameter of from about 30 to about 50 mm. In regard to the shape of condoms now marketed, the relatively low elastic modulus of natural rubber at 30% extension, in the range of from 30 to 50 psi allows a very wide range of the population to comfortably utilize a single product of uniform shape. However, persons skilled in the art of condom manufacture know that suitable thermoplastic elastomers now available have a higher elastic modulus than natural rubber at 30% extension, i.e., in the range of from 80 to 150 psi. Thus, to enable a broader range of the population to comfortably employ the condom produced herein, it has been found advantageous to taper the condom in order to control the location in which the pressure caused by the strain of the condom during use is applied. Referring to FIG. 6, there is depicted a tapered condom in one embodiment contemplated herein. Specifically, the tapered condom herein has an axially centered tubular body, an open end and an opposite closed end, with the tubular body having a maximum diameter at a point along said axis adjacent to said closed end and with the tubular body having a minimum diameter at a point along said axis between said point of maximum diameter to and including the open end. The ratio of maximum diameter to minimum diameter should fall within the range of 1.05/1 to 1.4/1 and preferably between 1.1/1 to 1.25/1. The location of the point of maximum diameter is preferably immediately adjacent to the closed end of the condom. The location of the point of minimum diameter might be anywhere along the tubular body but preferably is closer to the open end of the condom than to the closed end. There may be multiple points of minimum diameter as where the condom tapers to a ribbed tubular body or the point of minimum diameter might comprise a segment of the tubular body with a constant diameter. For a condom having an elastic modulus within the range stated immediately above, it has been found that the most advantageous dimensions for a condom having utility for the widest range of the population are 37–40 mm diameter at the minimum tapered to 40–45 mm diameter at the maximum. The tapered condom may be produced utilizing a tapered mold in the drawing of the condom and/or by annealing the condom on a tapered mandrel.

A bead may be incorporated onto the condom at its open end in order to insure its retention in use and to facilitate handling and rolling of the condom. The bead may be installed by two methods. In the first method, the condom is placed on a mandrel former, the excess material trimmed, the film rolled down to form a bead and the bead fused into a solid ring. In the second method, a ring bead is prepared in a separate operation and fastened at the rim of the condom by a thermal fusion or adhesion process. This second method is referred to as "importing the bead".

The following example for the manufacture of a condom is offered by way of illustration and not by way of limitation.

Apparatus

The equipment herein is divided into two major components, a preheating oven and a plug assisted vacuum forming unit. The oven was an insulated metal box with temperature controlled heating elements and exhaust fan to provide the desired ambient temperature conditions within the oven. Also located with the oven, were two (2) temperature controlled Mid-Infrared (Mid-IR) heaters with fused quartz emitter plates and a radiant energy of 40 W/cm$^2$ and each having a radiating surface area of 100 cm$^2$. A track with a servo/computer controlled shuttle system was provided in the lower part of the oven where the preforms, mounted in holders, could be horizontally transported into the oven for heating, and subsequently horizontally transported through the oven and mounted onto the vacuum forming unit. The vacuum forming unit was a female glass mold in the shape of a condom mounted about a vertical axis with the terminal end of the mold downward. The mold had a tapered geometry with the diameter increasing from the open end towards the terminal end. The mold had a total length of 260 mm, a diameter of 38.5 mm at the open end and reach a maximum diameter of 42 mm. The approximate volume of the mold was 311 cm$^3$. A single-stage, single-action vacuum pump was connected to the mold through a vacuum port mounted on the terminal end at the point where the mold intersects the vertical axis. The vacuum pump had a single-action volume of 590 ml, and could thus evacuate the mold in a single draw of the piston. The position of the piston was controlled via a computer controlled servo motor to provide a precise vacuum profile throughout the forming process. The mold was encapsulated by a jacket where a liquid was circulated to control the temperature of the mold at about 15° C. At the open end of the mold, there were two metal flaps and ancillary hardware that were capable of combining with the preform holder and sealably mounting the preform. A plug assembly comprising a metal rod and a frustoconically shaped contact element was axially mounted above the open end of the mold in such a manner that it was extensible into the mold. The position of the contact element was controlled by a computer controlled servo motor to provide a precise rate of displacement into the mold and controlled depth in the mold. The contact element was made of Teflon with a roughened surface (50 grit) and was axially aligned with the base upward and the crown face downward. The heights of the frustum was 10 mm, base diameter 31.33 mm and crown diameter 35 mm. Axially extending from the crown face was a contacting projection having a length of 6 mm.

Preparation of the Preform

A continuous sheet of the polyesterurethane, Estane® 58238-032P polyesterurethane (a registered trademark of The B. F. Goodrich Company), having the properties of Table I was extruded to a thickness of from about 1.0 to about 1.9 mm. From this continuous sheet were stamped circular discs of from about 25 to about 30 mm in diameter. The discs were conditioned for at least 24 hours at room temperature and a relative humidity in the range of from about 20% to about 30%. A circular preform was placed onto the metal holder, mounted horizontally on the guide track and automatically horizontally transported into the preheated 110° C. oven. The metal holder was such that the preform disc would sit on a 6.3 mm ledge with a 45 mm diameter opening such that the bulk of the preform was exposed on both the top and bottom face to allow rapid and uniform heating. The preform was then immediately exposed to the two (2) Mid-IR heaters with a peak wave length of 28 μm at a temperature of 750° C. One heater was located 35 mm above the preform and the other heater was located 35 mm below the preform. The heaters were in continuous operation, thus the duration of the IR exposure was controlled by the transport system. The preform was heated in this manner to a point where it began to soften and "sag" under its own weight. This occurred with a radiant heater exposure time of about 19 seconds. At this point, the temperature of the preform, as measured by a narrow band (7.92 μm) infrared thermometer, was approximately 230° C. After the preform was exposed to the radiant heaters, the preform was horizontally transported along the track through the preheated 110° C. oven, in a time of approximately 8 seconds, and into the vacuum drawing apparatus which was at about room temperature, and sealingly clamped into position at the mold opening.

Vacuum Drawing

Figure 5:
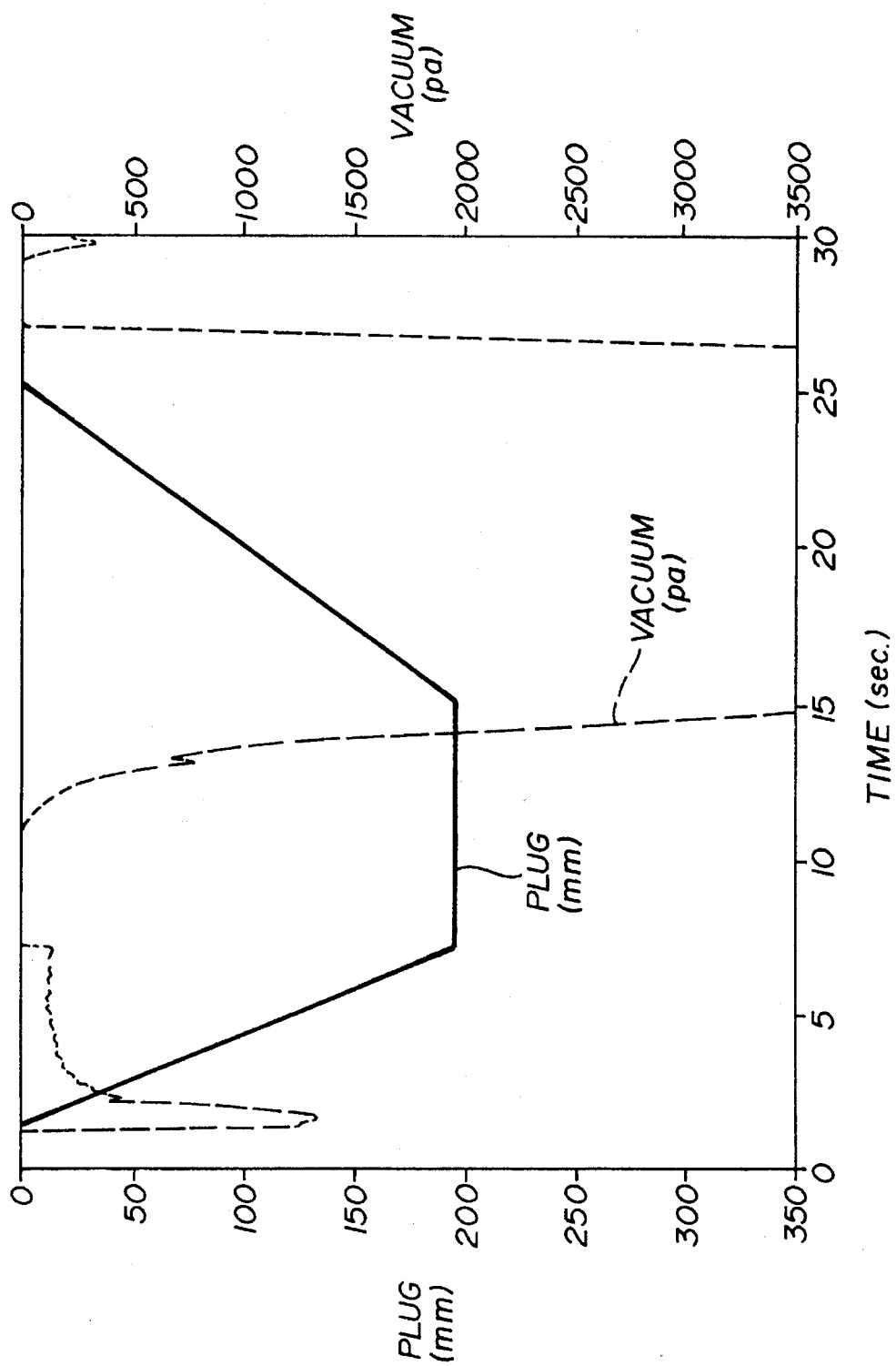
FIG. 5 is a tracing of mold cavity pressure as a function of time in the plug assisted drawing step where mold vacuum is employed.
Figure 7:
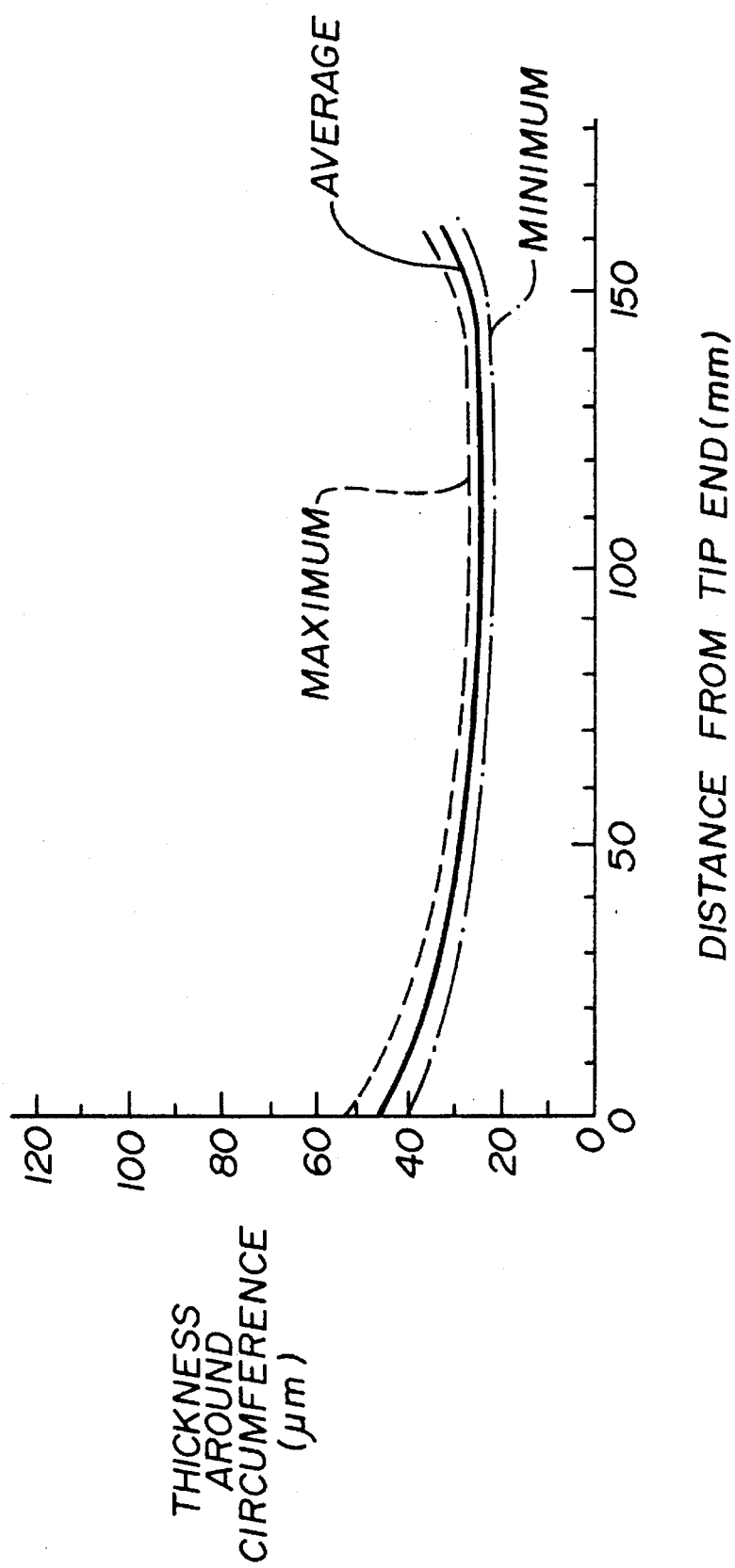
FIG. 7 is a plot of the thickness of a polyesterurethane condom wall made by the process herein as a function of distance from the tip end, where the reported thickness is the maximum, minimum and average for the circumference at each distance.
Figure 8:
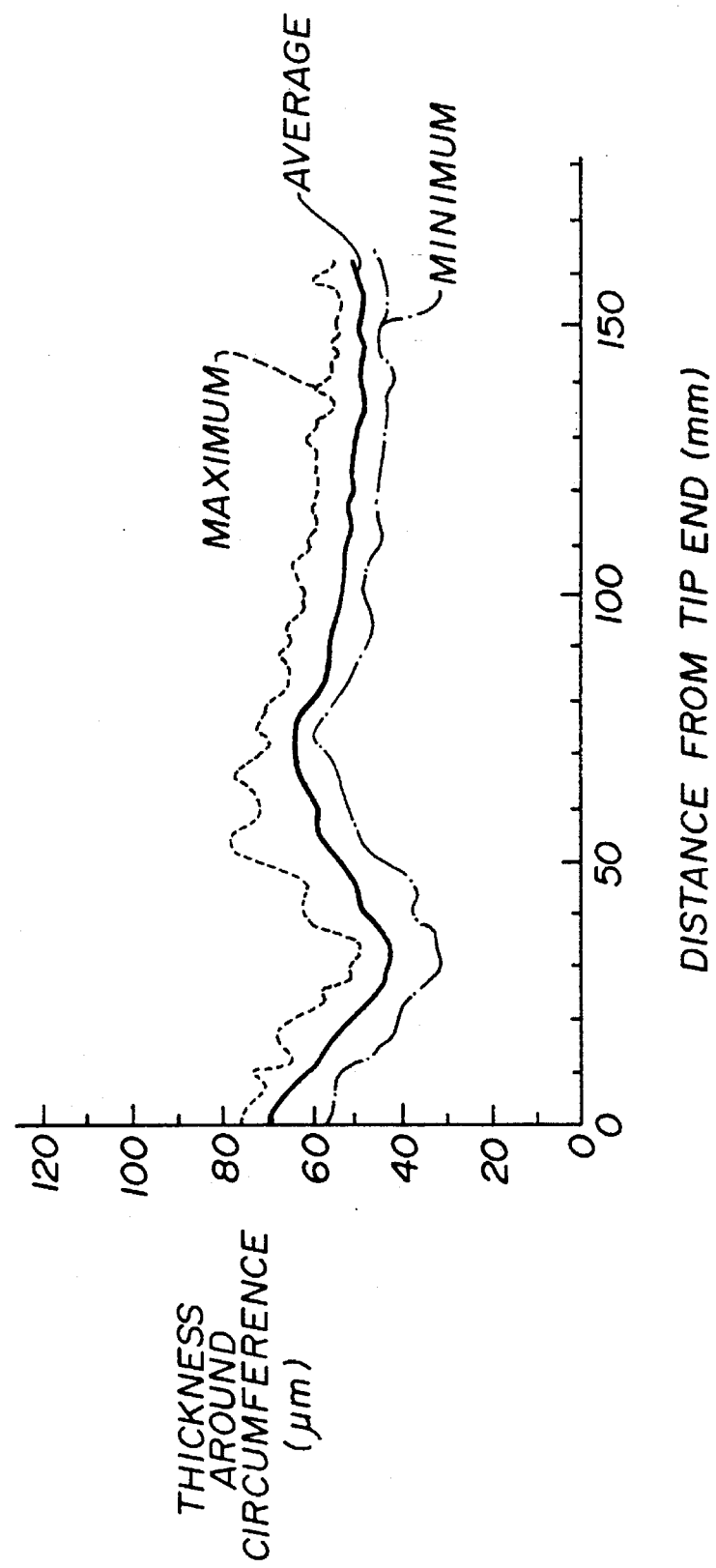
FIG. 8 is a plot of the thickness of a natural rubber condom wall made by a dipping process as a function of distance from the tip end, where the reported thickness is the maximum, minimum and average for the circumference at each distance.

The plug assisted vacuum drawing operation was initiated with initiation of plug extension. The elapsed time from the moment that the preform left the oven to the moment that forming began was about 2 seconds. The plug displacement profile was controlled by computer in the range of from about 30 to about 50 mm/sec. FIG. 5 is a representative plot of mold pressure and plug extension as a function of time during the vacuum forming. At about, or immediately before, the moment the plug contacted the hot preform, the vacuum was applied to act concurrently with the pushing action of the plug. The vacuum drawn condom was subsequently removed from the mold and annealed at 130° C. for 4 hours. FIG. 7 is a representative plot of thickness as a function of surface distance from the tip end for a condom as made above. FIG. 8 is a similar plot for a natural rubber condom produced from latex by a dipping process.

What is claimed is:

1. A condom formed from a polyesterurethane thermoplastic elastomer, said elastomer characterized by a melt index, measured at 210° C. under a 3800 g test load, in the range of from 24–36 g/10 min; 10–25% by weight MDI; 0.1–5% by weight 1,4-butanediol; 70–89.9% by weight polybutylene/hexylene adipate having an average molecular weight of 1000–3000 Daltons; and 0–5% by weight lubricant.

* * * * *